United States Patent [19]

Lertora et al.

[11] Patent Number: 4,555,525

[45] Date of Patent: Nov. 26, 1985

[54] USE OF DESETHYL-N-ACETYLPROCAINAMIDE (NAPADE) AS AN INOTROPIC AGENT

[75] Inventors: Juan J. L. Lertora; Lucy W. King, both of New Orleans, La.

[73] Assignee: Administrators of the Tulane Educational Fund, New Orleans, La.

[21] Appl. No.: 646,191

[22] Filed: Aug. 31, 1984

[51] Int. Cl.[4] .............................................. A61K 31/16
[52] U.S. Cl. ................................................. 514/616
[58] Field of Search ......................................... 514/616

[56] References Cited

U.S. PATENT DOCUMENTS 4,420,568 12/1983 Wang et al. ..................... 436/536

OTHER PUBLICATIONS

Ruo et al., Therapeutic Drug Monitoring 3: 231–237, 1981 (not attached).
Ruo et al., J. of Phar. and Ex. Ther., 216: 357–362, 1981 (not attached).
Goodman and Gilman: *The Pharmacological Basis of Therapeutics*, 5th Ed., MacMillan Pub., Chap. 32, pp. 683–704.

*Primary Examiner*—Douglas W. Robinson
*Attorney, Agent, or Firm*—Cushman, Darby & Cushman

[57] ABSTRACT

Heart failure and other heart abnormalties are treated with the inotropic agent desethyl-N-acetylprocainamide (NAPADE).

1 Claim, 4 Drawing Figures

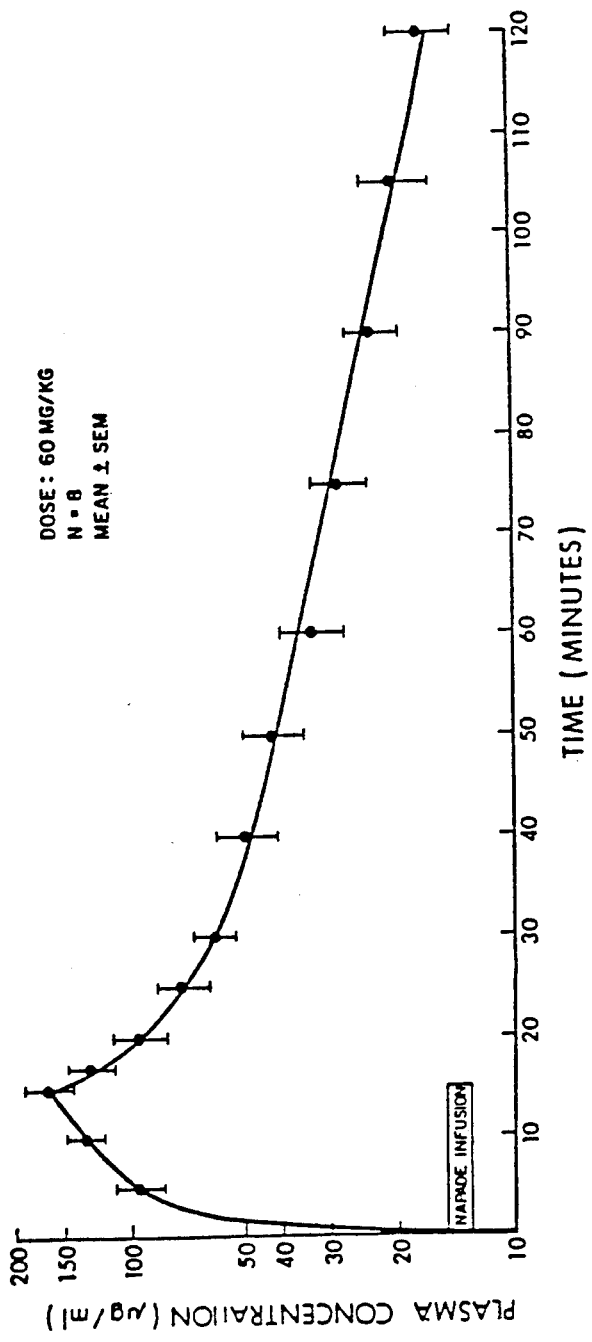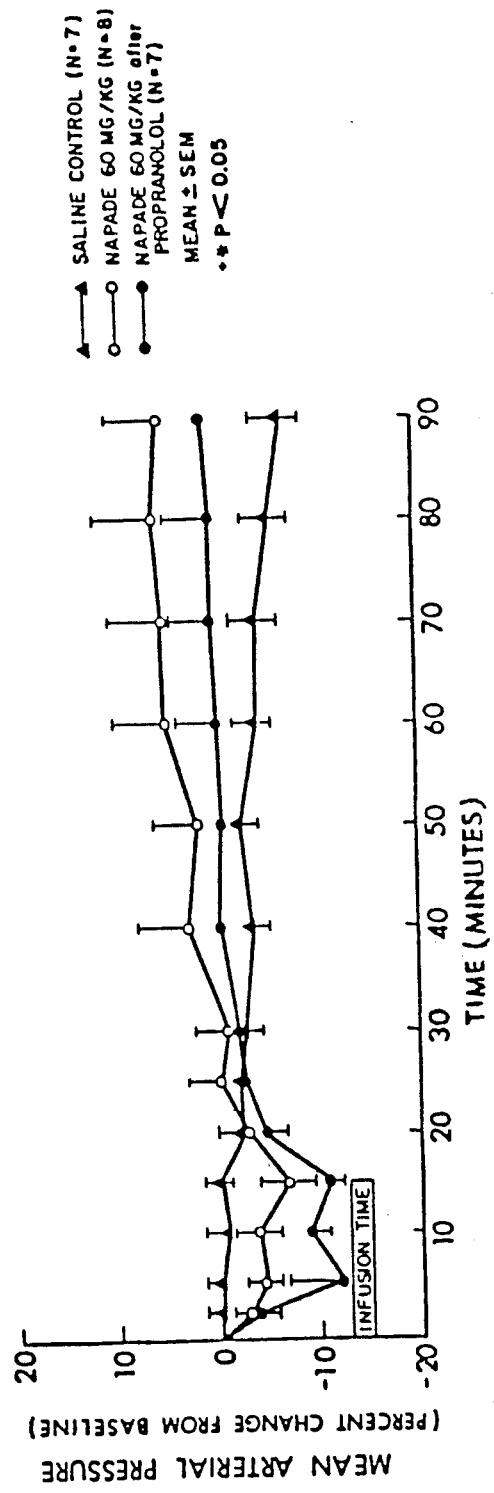

USE OF DESETHYL-N-ACETYLPROCAINAMIDE (NAPADE) AS AN INOTROPIC AGENT

BACKGROUND OF THE INVENTION

This invention relates to the treatment of heart abnormalities and in particular to a method of increasing the force of contraction of the cardiac muscle (positive inotropic effect) and increasing the heart rate (positive chronotropic effect) without decreasing blook pressure (hypotensive effect) using NAPADE, a naturally occurring metabolite of procainamide and N-acetylprocainamide. The method is particularly suited for treating patients experiencing heart failure to increase the force of contraction of the heart muscle and in the treatment of cardiac arrhythmias.

Procainamide is a well known, widely prescribed compound used in the treatment of premature ventricular contractions and ventricular tachycardia, atrial fibrillation, and paroxysmal tachycardia. The primary use of procainamide is in the therapy of atrial fibrillation and other cardiac arrhythmias; see Goodman and Gilman, The Pharmacological Basic of Therapeutics, 5th Edition, 1975, Chapter 32, Antiarrhythmic Drugs.

Procainamide has the formula:

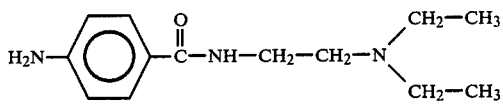

Desethyl-N-acetylprocainamide (NAPADE), also known as desethyl acecainide, has the structural formula:

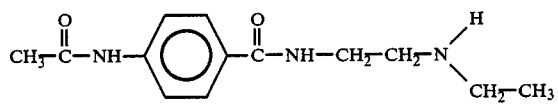

a molecular weight of 249, and is a naturally occurring metabolite of procainamide and N-acetylprocainamide (NAPA). NAPADE was first described by Dreyfuss et al: Metabolism of Procainamide in Rhesus Monkeys and Man, Clin. Pharmacol. Ther. 13:366-367 (1972) and later identified as a metabolite in humans treated with procainamide and NAPA by Taber et al: N-Desethylacecainide Is a Metabolite of Procainamide in Man, Drug Metab. Dispos. 7:346 (1979) and Ruo et al: Plasma Concentrations of Desethyl-N-acetylprocainamide in Patients Treated with Procainamide and N-acetylprocainamide, Ther. Drug. Monitor. 3:231-237 (1981). NAPADE was reported by Ruo to exhibit antifibrillatory activity in mice; Identification of Desethyl Procainamide in Patients: A New Metabolite of Procainamide, J. Pharmacol. Exp. Ther. 216:357-362 (1981).

BRIEF DESCRIPTION OF THE DRAWINGS

FIG. 1 is a graph comparing NAPADE plasma concentration following infusion over a period of 120 minutes; and FIGS. 2-4 report the percentage change in myocardial force, heart rate and mean arterial pressure, respectively, over a period of 90 minutes.

DETAILED DESCRIPTION OF THE INVENTION

Figure 2:
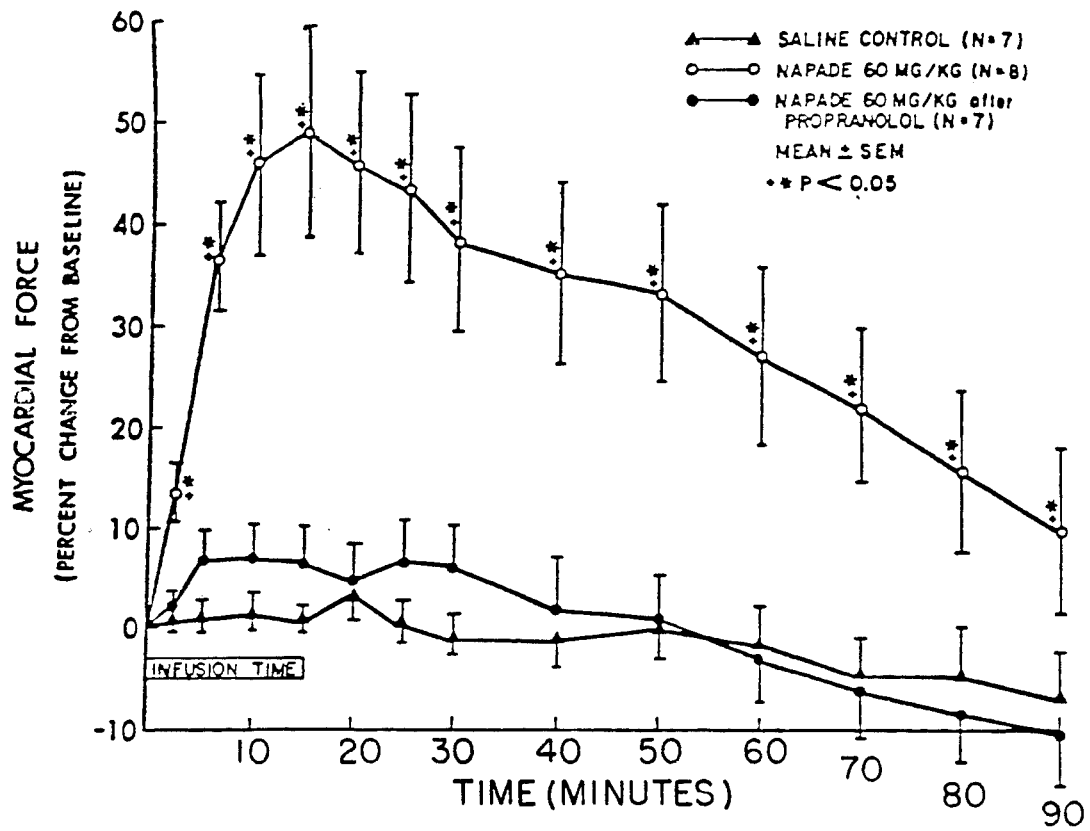

We have investigated the cardiovascular effects of NAPADE in animal models and have observed the following unique properties of NAPADE:

(a) NAPADE has a positive inotropic effect—it increases the force of contraction of the cardiac muscle;

(b) NAPADE has a positive chronotropic effect—it increases heart rate; and (c) NAPADE lacks significant hypotensive effects.

In contrast to these observations, procainamide decreases the force of contraction of the heart muscle, decreases the heart rate and exhibits hypotensive effects—it lowered the blood pressure. NAPA increases the force of contraction of heart muscle but is otherwise similar to procainamide in decreasing the heart rate and exhibiting hypotensive effects. These experiments also demonstrated that pretreatment with propranolol, a $\beta$-adrenergic receptor blocker, abolishes the positive inotropic and chronotropic actions of NAPADE; NAPADE lacks negative inotropic effects in the presence of $\beta$-adrenergic receptor blockade with propranolol, i.e., NAPADE does not depress the cardiac muscle; only a mild decrease in blood pressure is seen when NAPADE is given after propranolol pretreatment.

In addition to the above, we propose that NAPADE can be an effective antiarrhythmic for use in patients with cardiac arrhythmias and myocardial dysfunction, since it does not have the risk of inducing myocardial depression and heart failure. NAPADE is believed to be useful as an inotropic agent, even if it lacked antiarrhythmic efficacy, given the very significant increase in myocardial force of contraction that was observed in our studies. The administration of NAPADE to patients experiencing heart failure in order to increase the force of contraction of the heart is a central aspect of the present invention.

NAPADE is available as the hydrocholoride salt, however pharmaceutically acceptable salts and alternate drug delivery systems are within the scope of this invention.

At equal doses (60 mg/kg given i.v. as a 15 minute infusion), the parent drug procainamide has a negative inotropic effect (it decreases the force of contraction of the cardiac muscle), which is the opposite of our finding with NAPADE. Furthermore, although NAPA (N-acetylprocainamide) also has positive inotropic effects, a negative inotropic action is apparent when NAPA is given after pretreatment with propranolol. No such effect was seen with NAPADE, suggesting that it lacks intrinsic mycardial depressant actions. NAPADE is a procainamide derivative with positive inotropic effects which is important in patients requiring antiarrhythmic therapy, or patients suffering from myocardial dysfunction or heart failure, in whom a negative inotropic effect would be undesirable.

Pharmacokinetic studies in chloralose-urethane anesthetized dogs indicated that NAPADE has a short elimination half-life of approximately 60 minutes, thus intravenous injection, preferably continuous intravenous infusion, is the preferred route of administration.

The invention will be further explained with reference to the following illustrative example.

EXAMPLE

Male mongrel dogs (12-21 kg) received chloralose-urethane anesthesia and underwent a medial sternotomy to expose the heart. The dogs were then instrumented for the recording of heart rate, arterial pressure and right ventricular myocardial force (using Walton-Brodie gauge).

Saline (N-7), NAPADE-HCl 60 mg/kg (N-8) or NAPADE-HCl 60 mg/kg after pretreatment with propranolol (0.5 mg/kg followed by 10 μg/kg/min) (N-7) were given as a 15-minute IV infusion. Blood samples were obtained over a period of 5–120 minutes to measure NAPADE plasma concentration by high-performance liquid chromatography (HPLC) and to construct a plasma concentration versus time curve of FIG. 1.

The pharmacokinetics of NAPADE were analyzed with a two-compartment model with elimination from the central compartment. The method of residuals was used to resolve the exponential components of each plasma concentration versus time curve and to obtain estimates of alpha and beta (first-order rate constants) and A and B intercepts corrected to 0-time using the method of Loo and Reigelman. These parameters were then used to estimate apparent volume of distribution ($V_{central}$, $V_{peripheral}$, $V_{total}$) and clearance values ($Cl_{intercompartmental}$, $Cl_{elimination}$) for each dog according to standard pharmacokinetic methodology.

Myocardial force, mean arterial pressure and heart rate are expressed as the percent change from baseline for each experimental group. Statistical analysis was done with analysis of variance for repeated measurements and Duncan's multiple range test. All values are mean ± SEM.

Discussion of the results: Under the conditions of our assay, an excellent resolution was obtained between NAPADE, NAPA and the internal standard (NAPA, N-propionylprocainamide) (FIG. 2).

In the pharmacokinetic analysis, the infusion of NAPADE-HCl 60 mg/kg resulted in peak NAPADE concentrations of 164.7±18.1 μg/ml at 15 minutes. NAPADE concentrations then declined in a bi-exponential fashion as shown in FIG. 1, with a terminal half-life (T½ beta) of 54.5±2.9 minutes. Volume and clearance parameters for a two-component model are shown in the following table.

Figure 3:
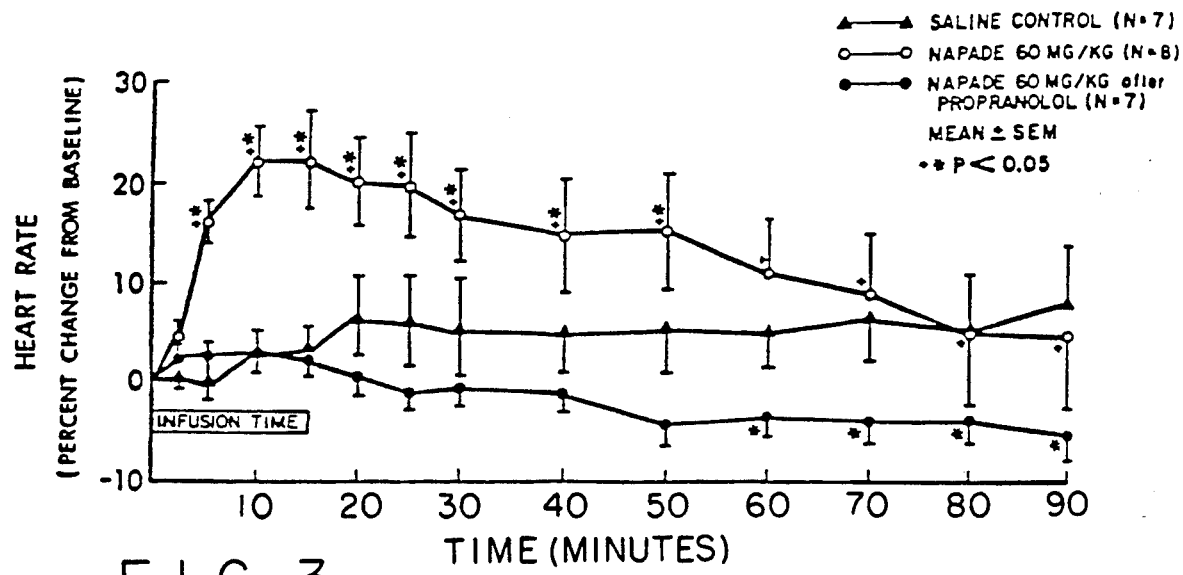

Cardiovascular actions: The infusion of NAPADE resulted in significant increases in myocardial force and heart rate, with small and statistically insignificant changes in blood pressure. Peak effects coincided with peak plasma concentrations of NAPADE at 15 minutes. Myocardial force increased to a maximum of 48.9±10 percent over baseline and then declined linearly with time, remaining significantly increased for 90 minutes when compared to the control group (see FIG. 2). Heart rate increased to a maximum of 22.2±4.4 percent over baseline and then declined, remaining significantly increased over control for 50 minutes (see FIG. 3).

In the propranolol-treated group, adequacy of β-adrenergic receptor blockade was tested with standard doses of isoproterenol (0.025 and 0.05 μg/kg IV) given before and after the loading dose of propranolol. The inotropic, chronotropic and hypotensive actions of isoproterenol were effectively blocked.

Pretreatment with propranolol blocked the positive inotropic and positive chronotropic actions of NAPADE. In addition, propranolol pretreatment seemed to potentiate the mild hypotensive actions of NAPADE (see FIG. 4).

TABLE 1

| | NAPADE PHARMACOKINETICS IN THE DOG: TWO-COMPARTMENT MODEL | | | | | |
|---|---|---|---|---|---|---|
| DOG No. | $V_{CENTRAL}$ (L/KG) | $V_{PERIPHERAL}$ (L/KG) | $V_{TOTAL}$ (L/KG) | $Cl_{INTERC.}$ (L/MIN/KG) | $Cl_{ELIMINATION}$ (L/MIN/KG) | $T_{\frac{1}{2}(BETA)}$ (MINUTES) |
| 1 | 0.188 | 0.258 | 0.447 | 0.00746 | 0.00817 | 55 |
| 2 | 0.104 | 0.237 | 0.342 | 0.00999 | 0.00499 | 60 |
| 3 | 0.159 | 0.733 | 0.893 | 0.02467 | 0.01261 | 67 |
| 4 | 0.212 | 0.264 | 0.476 | 0.00991 | 0.00734 | 57 |
| 5 | 0.219 | 0.586 | 0.806 | 0.02412 | 0.01311 | 56 |
| 6 | 0.111 | 0.388 | 0.499 | 0.02245 | 0.01154 | 40 |
| 7 | 0.090 | 0.203 | 0.293 | 0.00931 | 0.00575 | 47 |
| 8 | 0.137 | 0.208 | 0.346 | 0.01577 | 0.00500 | 54 |
| MEAN | 0.153 | 0.360 | 0.513 | 0.01546 | 0.00856 | 54.5 |
| SEM | 0.017 | 0.069 | 0.078 | 0.00257 | 0.00120 | 2.9 |

PARAMETERS:
VOLUME OF THE CENTRAL COMPARTMENT ($V_{CENTRAL}$)
VOLUME OF THE PERIPHERAL COMPARTMENT ($V_{PERIPHERAL}$)
TOTAL APPARENT VOLUME OF DISTRIBUTION ($V_{TOTAL}$)
INTERCOMPARTMENTAL CLEARANCE ($Cl_{INTERC.}$)
ELIMINATION CLEARANCE ($Cl_{ELIMINATION}$)
ELIMINATION HALF-LIFE (T½ BETA)
VOLUME AND CLEARANCE VALUES ARE NORMALIZED TO DOG'S BODY WEIGHT (RANGE 12-18 KG).

Our observations may be summarized as follows: 1. NAPADE has significant positive inotropic and chronotropic actions in the chloralose-urethane anesthetized dog. These actions occur without significant changes in systemic arterial pressure. 2. Peak inotropic and chronotropic actions correlated with peak plasma concentrations of NAPADE at 15 minutes. The inotropic and chronotropic actions were long-lasting (50–90 minutes) and declined linearly with time following the end of the NAPADE infusion. 3. β-adrenergic receptor blockade with propranolol effectively blocked the positive inotropic and chronotropic actions of NAPADE, suggesting that these actions are indirect and catecholamine-mediate. Propranolol pretreatment also potentiated the mild hypotensive actions of NAPADE. 4. NAPADE exhibited bi-exponential kinetics of elimination suitable for two-compartment analysis. Its apparent volume of distribution ($V_{total}$=0.513±0.078 L/kg) is approximately one-third of the value obtained in previous studies with NAPA (1.48±0.16 L/kg). On the other hand, NAPADE's elimination clearance (0.00856±0.00120 L/min/kg) is approximately three times larger than NAPA's clearance in the dog (0.00264±0.00090 L/min/kg). Thus, the observed elimination half-life (T½ beta) of 54.5±2.9 minutes of NAPADE is considerably shorter than the half-life of NAPA in the dog (approximately six hours).

We claim:

1. A method of increasing the force of contraction of cardiac muscle in an animal requiring same comprising administering to said animal an inotropic effective amount of desethyl-N-acetylprocainamide or a pharmaceutically acceptable salt thereof.

* * * * *